US011412730B2

(12) United States Patent
De Larichaudy

(10) Patent No.: US 11,412,730 B2
(45) Date of Patent: Aug. 16, 2022

(54) METHOD FOR THE CRYOPRESERVATION OF CELLS FOR THERAPEUTIC PURPOSES

(71) Applicant: LABORATOIRE FRANCAIS DU FRACTIONNEMENT ET DES BIOTECHNOLOGIES, Les Uli (FR)

(72) Inventor: Joffrey De Larichaudy, Malakoff (FR)

(73) Assignee: LABORATOIRE FRANCAIS DU FRACTIONNEMENT ET DES BIOTECHNOLOGIES, Les Ulis (FR)

(*) Notice: Subject to any disclaimer, the term of this patent is extended or adjusted under 35 U.S.C. 154(b) by 504 days.

(21) Appl. No.: 15/737,469

(22) PCT Filed: Jun. 30, 2016

(86) PCT No.: PCT/FR2016/051629
§ 371 (c)(1),
(2) Date: Dec. 18, 2017

(87) PCT Pub. No.: WO2017/001782
PCT Pub. Date: Jan. 5, 2017

(65) Prior Publication Data
US 2019/0000070 A1    Jan. 3, 2019

(30) Foreign Application Priority Data
Jun. 30, 2015 (FR) .................................. 1556167

(51) Int. Cl.
| *A01N 1/02*  | (2006.01) |
| *A61K 47/20* | (2006.01) |
| *A61K 47/26* | (2006.01) |
| *A61K 47/42* | (2017.01) |
| *A61K 35/33* | (2015.01) |
| *A61K 35/34* | (2015.01) |
| *A61K 38/38* | (2006.01) |
| *A61K 35/15* | (2015.01) |
| *A61K 35/17* | (2015.01) |
| *A61K 9/00*  | (2006.01) |
| *A61K 47/18* | (2017.01) |
| *A61K 35/14* | (2015.01) |
| *A61K 35/28* | (2015.01) |

(52) U.S. Cl.
CPC .......... *A01N 1/0221* (2013.01); *A61K 9/0019* (2013.01); *A61K 35/14* (2013.01); *A61K 35/15* (2013.01); *A61K 35/17* (2013.01); *A61K 35/28* (2013.01); *A61K 35/33* (2013.01); *A61K 35/34* (2013.01); *A61K 38/38* (2013.01); *A61K 47/183* (2013.01); *A61K 47/20* (2013.01); *A61K 47/26* (2013.01); *A61K 47/42* (2013.01)

(58) Field of Classification Search
CPC .... A61K 2300/00; A61K 35/15; A61K 35/17; A61K 35/33; A61K 35/34; A61K 38/38; A61K 35/14; A61K 35/28; A61K 47/183; A61K 47/20; A61K 47/26; A61K 47/42; A61K 9/0019; A01N 1/0221
See application file for complete search history.

(56) References Cited

U.S. PATENT DOCUMENTS

| 2004/0209235 | A1  | 10/2004 | Goldstein et al. |
| 2005/0026133 | A1  | 2/2005  | Nakatsuji et al. |
| 2006/0073591 | A1* | 4/2006  | Abitorabi ............. C12N 5/0037 435/404 |
| 2010/0158873 | A1  | 6/2010  | Pinset |
| 2017/0051252 | A1  | 2/2017  | Morgan et al. |
| 2018/0187150 | A1* | 7/2018  | De Larichaudy .... A01N 1/0221 |

FOREIGN PATENT DOCUMENTS

| JP | 2006-115837 A  | 5/2006  |
| WO | 91/12718 A1    | 9/1991  |
| WO | 2006/092668 A2 | 9/2006  |
| WO | 2006/124875 A2 | 11/2006 |
| WO | 2012/001075 A2 | 1/2012  |

OTHER PUBLICATIONS

Golab, K. et al., "Challenges in cryopreservation of regulatory T cells (Tregs) for clinical therapeutic applications," International Immunopharmacology 16 (2013) 371-375.
Holloway, P.A. et al., "Antigens shared by malignant plasma cells and normal B cells may be involved in graft versus myeloma," Clin Exp Immunol 2003; 131:340-346.
Huang, J. et al., "Combining ovarian tissue cryobanking with retrieval of immature oocytes followed by in vitro maturation and vitrification: an additional strategy of fertility preservation," Fertility and Sterility, vol. 89, No. 3, Mar. 2008.
Ikarashi, H. et al., "Solid-phase Anti-CD3 Antibody Activation and Cryopreservation of Human Tumor-infiltrating Lymphocytes Derived from Epithelial Ovarian Cancer," Jpn. J. Cancer Res. 83, 1359-1365, Dec. 1992.
Letessier, E. et al., "Enrichment in Tumor-reactive CD8+ T-Lymphocytes by Positive Selection from the Blood and Lymph Nodes of Patients with Head and Neck Cancer," Cancer Research 51, 3891-3899, Aug. 1, 1991.
"MediCult Vitrification Warming," Retrieved Apr. 5, 2016: http://www.origio.com/en/products/art-media/medicult-vitrification-warming.
Smagur, A. et al., "Impact of different dimethyl sulphoxide concentrations on cell recovery, viability and clonogenic potential of cryopreserved peripheral blood hematopoietic stem and progenitor cells," Vox Sanguinis (2013) 104, 240-247.
Smagur, A. et al., "Comparison of the cryoprotective solutions based on human ablumin vs. autologous plasma: its effect on cell recovery, clonogenic potential of peripheral blood hematopoietic progenitor cells and engraftment after autologous transplantation" Vox Sanguinis (2015) 108, 417-424.

(Continued)

Primary Examiner — Blaine Lankford
(74) Attorney, Agent, or Firm — Nixon & Vanderhye

(57) ABSTRACT

Disclosed is a composition including, in a physiologically acceptable medium: a) human albumin; b) at least one saccharide; c) DMSO and L-cysteine or coenzyme Q10; and d) cells for therapeutic purposes, with the exception of specific tumour-infiltrating lymphocytes.

21 Claims, No Drawings

(56) References Cited

OTHER PUBLICATIONS

Lonza Technical_Data_Sheets_L_LZBE12-719F_C, DMEM: Ham's F-12 50:50 Mix.
Thumann, P. et al., "Antigen loading of dendritic cells with whole tumor cell preparations," Journal of Immunological Methods 277 (2003) 1-16.
Visioni, A. et al., "Expansion of melanoma-specific T cells from lymph nodes of patients in stage III: Implications for adoptive immunotherapy in treating cancer," Surgery, Oct. 2012, pp. 557-566.
SIGMA-ALDRICH: "Dulbecco s Modified Eagle s Medium/Ham s Nutrient Mixture F12", Dec. 1, 2006 (Dec. 1, 2006), XP009165985, Retrieved from the Internet <URL:http://www.sigmaaldrich.com/etc/medialib/docs/Sigma/Product_Information_Sheet/p5 6495.Par.0001.File.tmp/p56495.pdf> [retrieved on Apr. 21, 2016].
Yan Li et al: "Bioprocessing of Cryopreservation for Large-Scale Banking of Human Pluripotent Stem Cells", Bioresearch Open Access, vol. 1, No. 5, Oct. 1, 2012 (Oct. 1, 2012), pp. 205-214, XP055231320, ISSN: 2164-7860, DOI: 10.1089/biores.2012.0224.
David Berz et al: "Cryopreservation of hematopoietic stem cells", American Journal of Hematology, vol. 82, No. 6, Jun. 1, 2007 (Jun. 1, 2007), pp. 463-472, XP055107084, ISSN: 0361-8609, DOI: 10.1002/ajh.20707.
Charles J. Hunt: "Cryopreservation of Human Stem Cells for Clinical Application: A Review", Transfusion Medicine and Hemotherapy, vol. 38, No. 2, Jan. 1, 2011 (Jan. 1, 2011), CH, pp. 107-123, XP055236379, ISSN: 1660-3796, DOI: 10.1159/000326623.
Akalabya et al.: "Effects of non-toxic cryoprotective agents on the viability of cord blood derive MNCS", Department of Biotechnology and Medical Engineering, National Instutute of Technology Rourkela, India, pp. 453-465 (2013).
International Search Report, dated Sep. 23, 2016, from corresponding PCT/FR2016/051629 application.

* cited by examiner

METHOD FOR THE CRYOPRESERVATION OF CELLS FOR THERAPEUTIC PURPOSES

The present invention relates to a composition comprising, in a physiologically acceptable medium:
a) human serum albumin,
b) at least one saccharide,
c) DMSO and L-cysteine or coenzyme Q10, and
d) cells for therapeutic purposes, with the exception of specific tumor-infiltrating lymphocytes.

The present invention also relates to a process for the cryopreservation of at least one sample of cells for therapeutic purposes, with the exception of specific tumor-infiltrating lymphocytes, comprising the following steps:
i) mixing the sample of cells for therapeutic purposes with:
   a) human serum albumin,
   b) at least one saccharide, and
   c) DMSO and L-cysteine or coenzyme Q10, then
ii) freezing the mixture obtained in step i).

Cryopreservation is a process in which biological samples are stored at low temperature. The cryopreservation of biological material is generally carried out by freezing said material, in an appropriate support, such as a tube or a vial made of glass or plastic material (generally referred to as a "straw" or cryotube in the field of cryopreservation), said support being suitable for long-term storage at low temperature.

However, cryopreservation poses a certain number of problems and technical constraints. Cell damage may especially arise during the thawing, leading to apoptosis or the bursting of the cells. In addition, the survival of cryopreserved cells may depend on the conditions and techniques used during the freezing. Controlling the rate of cooling is important: cooling at a low rate enables ordered crystallization of the freezable water outside the cells—the cells become dehydrated, shrink, and the water leaves the cell. In the opposite scenario, the formation of intracellular ice leads to the destruction of membrane structures, which is lethal for the cell.

For the majority of mammalian cells, as is the case for products and medications for cell therapy, whether the cells are genetically modified or not, it is also vital to use cryo-protectants in order to preserve cell integrity and functionality.

Currently, manufacture on an industrial scale (European or worldwide, especially) of products for cell therapy poses new problems, such as the stability of the finished product administered and variability linked to the starting biological material.

In the majority of cases, the finished product is packaged:
fresh in a liquid medium (of albumin or saline solution type) with preservation limited to a few hours or days, or else
frozen in a simple formulation based on DMSO, which is not very stable and not very effective in the long term. The not inconsiderable amount of dead cells, of debris with potentially immunogenic effects, and the toxicity for the patient of the excipients commonly used are all limiting factors. Washing the cells before administration to remove these toxic elements (whether biological or not) is commonly advised: these solutions are not compatible with distribution on an industrial scale. Moreover, they do not afford much flexibility in terms of administration and storage, unlike other "conventional" classes of medication.

There is therefore a need to develop a product and/or medication for cell therapy which is stable in the long term (i.e. for several months), which is easy to use, which can be directly injected, and which is non-toxic.

The present invention makes it possible to meet this need. Indeed, the composition according to the invention makes it possible to obtain products for cell therapy comprising cells for therapeutic purposes, which are ready to use (i.e. ready to be injected without washing, which avoids all additional handling operations causing decreased viability and loss of cells), stable in the long term, easy to use, and non-toxic.

The present invention therefore relates to a composition comprising, in a physiologically acceptable medium:
a) human albumin (or human serum albumin),
b) at least one saccharide,
c) DMSO and L-cysteine or coenzyme Q10, and
d) cells for therapeutic purposes, with the exception of tumor-infiltrating lymphocytes,
said tumor-infiltrating lymphocytes being obtained by in vitro culture of tumor-infiltrating lymphocytes from a sample taken of in-transit, lymph-node or metastatic cutaneous nodules from a patient suffering from a stage 3 or 4 melanoma, said culture comprising the emergence (also referred to as the "exit" or the "primary culture") of said tumor-infiltrating lymphocytes contained in the sample taken of in-transit, lymph-node or metastatic cutaneous nodules, then the stimulation of the tumor-infiltrating lymphocytes resulting from the emergence step, then finally the amplification of the stimulated tumor-infiltrating lymphocytes.

These tumor-infiltrating lymphocytes (also referred to as TILs) are obtained by in vitro culture of tumor-infiltrating lymphocytes from a sample taken of in-transit, lymph-node or metastatic cutaneous nodules from a patient suffering from a stage 3 or 4 melanoma, said culture comprising:
emergence of said tumor-infiltrating lymphocytes contained in the sample taken of in-transit, lymph-node or metastatic cutaneous nodules. This emergence is also referred to as "primary culture" or "exit"; it is the step during which the tumor-infiltrating lymphocytes, initially contained in the sample taken of in-transit, lymph-node or metastatic cutaneous nodules, move into the culture medium and are cultured in vitro, then
stimulation of the tumor-infiltrating lymphocytes resulting from the emergence step, then finally
amplification of the stimulated tumor-infiltrating lymphocytes.

Such TILs are referred to as "specific tumor-infiltrating lymphocytes" in the present application.

The present invention also relates to a process for the cryopreservation of at least one sample of cells for therapeutic purposes, with the exception of specific tumor-infiltrating lymphocytes, comprising the following steps:
i) mixing the sample of cells for therapeutic purposes with:
   a) firstly human albumin, then
   b) at least one saccharide, and c) DMSO and L-cysteine or coenzyme Q10, then
ii) freezing the mixture obtained in step i).

The present invention also relates to the use of a composition comprising, in a physiologically acceptable medium:
a) human albumin,
b) at least one saccharide, and
c) DMSO and L-cysteine or coenzyme Q10, for the cryopreservation of at least one sample of cells for therapeutic purposes, with the exception of specific tumor-infiltrating lymphocytes.

In the present application, the specific tumor-infiltrating lymphocytes excluded from the composition according to the invention are autologous; they correspond to the tumor-infiltrating lymphocytes contained in the tumor(s).

These tumor-infiltrating lymphocytes excluded from the present invention are obtained by in vitro culture of tumor-infiltrating lymphocytes from a sample taken of in-transit, lymph-node or metastatic cutaneous nodules from a patient suffering from a stage 3 or 4 melanoma, said culture comprising:

emergence of said tumor-infiltrating lymphocytes contained in the sample taken of in-transit, lymph-node or metastatic cutaneous nodules. This emergence is also referred to as "primary culture" or "exit"; it is the step during which the tumor-infiltrating lymphocytes, initially contained in the sample taken of in-transit, lymph-node or metastatic cutaneous nodules, move into the culture medium and are cultured in vitro, then stimulation of the tumor-infiltrating lymphocytes resulting from the emergence step, then finally amplification of the stimulated tumor-infiltrating lymphocytes.

In particular, the step of emergence of the TILs may be carried out by primary culture of the sample taken of in-transit, lymph-node or metastatic cutaneous nodules, especially by primary culture in a selective culture medium without serum, of X-VIVO 15® type (sold by Cambrex Corp), supplemented with interleukin-2 (IL-2).

After emergence of the TILs, the latter undergo a step of stimulation, preferably in a compartmentalized closed culture container, especially in the presence at least of non-proliferating irradiated allogeneic feeder cells. "Closed culture container" is intended to mean a system which makes it possible to maintain cells in culture in a suitable medium, without said cells being directly in contact with the external environment. Finally, the step of stimulating the TILs is followed by an amplification step.

Preferably, all the TILs are excluded from the cells for therapeutic purposes of the present application.

The composition according to the invention therefore comprises, in a physiologically acceptable medium:
a) human albumin,
b) at least one saccharide,
c) DMSO and L-cysteine or coenzyme Q10, and
d) cells for therapeutic purposes, with the exception of specific tumor-infiltrating lymphocytes.

"Physiologically acceptable medium" is intended to mean an aqueous medium comprising electrolytes. Electrolytes are, for example, salts of sodium, potassium, magnesium, and/or calcium, with anions of chloride, carbonate, hydroxide or caprylate type. The physiologically acceptable medium is preferably an aqueous medium comprising sodium chloride and sodium caprylate.

The composition according to the invention comprises human serum albumin (human albumin or compound a)). This protein is a high molecular weight (approximately 65 kDa) plasma protein. It is the most abundant protein in the plasma; the normal mean concentration thereof is from 38 to 48 g/l. It makes it possible to buffer the pH and to maintain osmolarity. The purity thereof is preferably 95%. It is also possible to use one or more fragments and/or derivatives of human serum albumin, said fragments or derivatives being non-immunogenic and having an oncotic property similar to human serum albumin Preferably, the human serum albumin, the fragments and/or derivatives thereof, is present in an amount of between 2 and 10% by weight relative to the total weight of composition, preferably between 2.5 and 6% by weight, preferably between 3.5 and 4.5% by weight.

In the present application, unless indicated otherwise, the amounts are mentioned by weight relative to the total weight of composition.

The composition according to the invention also comprises at least one saccharide (compound b)). The saccharide improves cell survival and function by preserving osmotic equilibrium. A fraction penetrates the cells and makes it possible to stabilize the membrane structures. The saccharide is preferably selected from monosaccharides, disaccharides and trisaccharides.

The monosaccharides are preferably selected from glucose, galactose, fructose and mannose.

The disaccharide preferably has the formula A-B, wherein A and B are each independently selected from glucose, fructose and mannose. The saccharide is preferably a disaccharide. The disaccharide is preferably a glucose dimer. More preferentially, the disaccharide is selected from trehalose and sucrose. More preferentially, the disaccharide is trehalose.

The trisaccharides are preferably selected from raffinose (trimer of galactose, glucose and fructose), maltotriose and isomaltotriose (glucose trimers).

The saccharide is preferably present in the composition according to the invention at a concentration of between 0.05 M and 0.5 M, preferably between 0.07 M and 0.3 M, preferably between 0.08 M and 0.12 M.

The composition according to the invention finally comprises at least DMSO and L-cysteine or coenzyme Q10 (compounds c)). The composition according to the invention thus comprises, as compounds c), at least DMSO and L-cysteine. Alternatively, the composition according to the invention comprises, as compounds c), at least DMSO and coenzyme Q10.

DMSO, or dimethylsulfoxide, is a polar aprotic organic solvent of formula $CH_3-SO-CH_3$. It is an intracellular cryoprotectant, the main aim of which is to replace the intracellular liquid, and which thus makes it possible to prevent the formation of ice crystals and the osmotic stress inherent to the phases of freezing/thawing which cause membrane structures to burst. It is preferably present in the composition according to the invention in an amount of between 2 and 15% by weight, preferably between 2.5 and 4.5% by weight.

L-cysteine is an amino acid having a thiol group —SH. It is preferably present in the composition at a concentration of between 0.05 mM and 5 mM.

Coenzyme Q10, also referred to as ubiquinone, is a chemical compound comprising a quinone group. Its chemical name is 2,3-dimethoxy-5-methyl-6-decaprenylbenzoquinone. It is preferably present in the composition according to the invention in an amount of between 0.005 and 1% by weight, preferably between 0.007 and 0.5% by weight, preferably between 0.007 and 0.1% by weight.

The composition according to the invention preferably comprises, in a physiologically acceptable medium:
a) human albumin, preferably in an amount of between 2.5 and 6% by weight,
b) a saccharide, preferably trehalose, preferably at a concentration of between 0.05 M and 0.5 M, and
c) DMSO and L-cysteine, preferably respectively in an amount of between 2 and 15% by weight and in a concentration of between 0.5 mM and 2 mM.

The composition according to the invention is particularly beneficial, and aims to cryopreserve at least one sample of cells for therapeutic purposes. Indeed, the compounds a) to c) used in the composition according to the invention make it possible to sustainably and effectively cryopreserve cells for therapeutic purposes.

The cells for therapeutic purposes (compounds d)) are preferably chosen from:
- immune cells, such as NK cells, monocytes, B lymphocytes, T lymphocytes, which are natural or genetically modified, such as regulatory T lymphocytes, cytotoxic T lymphocytes, helper T lymphocytes, and chimeric antigen receptor (CAR) T lymphocytes;
- human myoblasts;
- hematopoietic stem cells;
- mesenchymal stem cells;
- cardiac cells;
- fibroblasts; and
- all other natural or genetically modified cells.

NK cells (or NK lymphocytes) are cells of innate immunity. They are non-T (CD3-), non-B (CD19-) lymphocytes, characterized in humans by the markers CD56, CD16 and NK.

Monocytes are leukocytes which evolve into macrophages, dendritic cells or osteoclasts.

B lymphocytes are immune cells responsible for the production of antibodies. Regulatory T lymphocytes are a sub-population of CD4+T lymphocytes, and inhibit the proliferation of other effector T lymphocytes.

Cytotoxic T lymphocytes are a sub-population of CD8+T lymphocytes, and destroy infected cells.

Helper T lymphocytes are a sub-population of CD4+T lymphocytes and mediate the immune response.

Finally, T lymphocytes having a chimeric antigen receptor (CAR), also referred to as CAR-T cells, correspond to a particular cell engineering technology. They are T lymphocytes which express a chimeric antigen receptor. CAR-T cells are capable of killing cancer cells by recognizing and binding to the tumor antigen present on said cancer cells.

The sample of cells for therapeutic purposes may originate from the patient to be treated (in this case the patient and the donor are the same person), by biopsy or taking a blood sample. In this case, the composition obtained, once cryopreserved then thawed, will be administered to this same patient: it is an autologous product. Alternatively, the sample of cells for therapeutic purposes may originate from another source (i.e. another individual or cell engineering), especially by biopsy or taking a blood sample. In this case, the composition obtained, once cryopreserved then thawed, will be administered to a patient to be treated, other than the donor: it is an allogeneic product.

The present invention also relates to a process for the cryopreservation of at least one sample of cells for therapeutic purposes, with the exception of specific tumor-infiltrating lymphocytes, comprising the following steps:
i) mixing the sample of cells for therapeutic purposes with:
  a) human albumin,
  b) at least one saccharide, and
  c) DMSO and L-cysteine or coenzyme Q10, then
ii) freezing the mixture obtained in step i).

In this process, the step of mixing i) the sample of cells for therapeutic purposes with the compounds a) to c) described above is typically carried out by dilution. The cells are preferably taken up in the compound a) in liquid form, preferably for 50% of the volume, then the compounds b) and c), preferably mixed together beforehand to obtain a 2× concentration solution, are added. The mixing of step i) may be carried out at around 4° C., or at room temperature (i.e. 20° C.).

As for the sample of cells for therapeutic purposes, it is preferably cultured beforehand in vitro, in a suitable culture medium. It then undergoes centrifugation, the supernatant is removed and the pellet is suspended in the compounds a), then b) and c) described above.

The step of freezing (step ii)) is preferably carried out over a drop in temperature from +4° C. or room temperature down to a temperature of between −100° C. and −160° C. The step of freezing (step ii)) is preferably carried out down to a temperature of between −100° C. and −180° C., preferably of between −140° C. and −160° C.

The sample is then stored at a temperature of generally less than −130° C.

Preferably, the freezing ii) is carried out by placing the mixture obtained in step i) in a container submerged in a mixture of isopropyl alcohol at +4° C., everything being brought to a temperature of between −70° C. and −90° C. This system ("freezing in a Nalgene box") enables, by virtue of the slow cooling of the alcohol, a virtually linear drop in temperature of between −1° C. and −2° C. per minute. Alternatively, preferably, the freezing ii) is carried out by means of a programmed freezer. Such freezers are in particular sold by Air Liquide or Cryobiosystem.

Preferably, the freezing ii) is carried out, especially by means of a programmed freezer, by the following steps:
- placing the mixture obtained in step i) at a temperature of +4° C.; then
- decreasing the temperature by 1° C. per minute from 4° C. to −40° C.; then
- decreasing the temperature by 10° C. per minute, from −40° C. to −150° C., to reach a final storage temperature of approximately −150° C.

The frozen product thus obtained may be kept for several months at approximately −150° C. These temperatures are those applied to the sample.

The invention is illustrated by the following wholly nonlimiting examples.

EXAMPLE 1: TESTS WITH THE FORMULATION ACCORDING TO THE INVENTION FOR CRYOPRESERVING MYOBLASTS

The following formulation, named 3.5% DMSO, was prepared:
3.5% DMSO+1 mM L-cysteine+0.1 M trehalose+4% human serum albumin (HA).

It requires an incubation time of 15 minutes maximum at 4° C. before freezing.

This complex formulation is combined with an automated temperature drop cycle carried out by means of a CRF (programmed freezer) which enables a complex drop in temperature according to a defined cycle. Down to −40° C. the cells are considered to be sensitive: the drop in temperature is slow and gradual to enable the formation of regular crystals. Below this threshold, the product is considered to be stable and the drop in temperature is rapid down to the storage temperature of −150° C. maximum (gaseous or liquid nitrogen).

Context of the Study

During the study of freezing of the myoblasts, 4 cycles were carried out, the characteristics of which are presented in the following table:

| Cycle (batch no.) | Starting material | Comments |
|---|---|---|
| 1 | Vials pass 1 | No control 10% DMSO |
| 2 | Vial pass 2 | No control 10% DMSO |
| 3 | Vial pass 2 | / |
| 4 | Vial pass 2 | / |

For these 4 cycles, vials of myoblasts originating from healthy patients were thawed. The cells were amplified then frozen at a concentration of $5 \times 10^6$ cells/ml by CRF.

In order to demonstrate the effectiveness of the freezing formulations, 3 arms were carried out. For each arm, 2 1 ml vials were thawed for testing.

|  | Arm 1 | Arm 2 | Arm 3 |
|---|---|---|---|
| Freezing Vials | 10% DMSO** 1A and 1B | CS10* 2A and 2B | 3.5% DMSO 4A and 4B |

*CS10: Cryostor 10, commercial freezing formulation (STEMCELL Technologies)
**10% DMSO + 4% HA.

Evaluation Criteria

With the aim of evaluating the effectiveness of the freezing formulations, different tests, presented in the following table, were carried out before freezing (referred to as T0) and after thawing. The results obtained with the thawed cells were compared to T0 and expressed in % of T0. This first analysis makes it possible to determine the effect of freezing on the cells, for each arm tested.

| T0 | Post-thawing | Aim |
|---|---|---|
| Viability | Viability at post-thawing Viability at 4 h post-thawing | General criterion (first criterion observed, often liberating, which enables or does not enable the injection to be correlated to effectiveness and to side-effects (increase in acellular impurities due to debris, aggregates etc.)). |
|  | Phenotype | Characterization of the cellular subpopulations and in particular the cells of interest. This is because the freezing/thawing cycle may specifically affect some more sensitive sub-types and alter the balance of the injected product (increase in cellular impurities). |
|  | Proliferation test | Determining the amplification factor of the cells, and hence their capacity for recovery, correlated to their metabolic/functional activity. |

Secondly, the different freezing arms were compared by statistical analysis. Since the reference freezing formulation commonly used within laboratories is 10% DMSO+4% HA, arm 1 served as reference for the statistical analysis. For cycles 1 and 2, arm 2 (freezing in CS10) served as a reference in the absence of cells formulated in 10% DMSO.

During the statistical analysis, the uniformity of variances was analyzed by a Fisher's test (F-test; uniform variance if p>0.05). A test of equality of means with two equal variance observations was carried out in the case of uniform variance. In the case of non-uniform variance by Fisher's test (p<0.05), a test of equality of means with two different variance observations was carried out. The means are not significantly different if p>0.10. The means are significantly different if p<0.10.

Results

Analysis of the Viability of the Cells

The analysis of the viability at 0 h post-thawing demonstrates that the percentages obtained upon thawing are equivalent to T0 for the arms 1, 2 and 3 (90 to 109% of T0).

For batch 1, the cells frozen in 3.5% DMSO have reduced viability compared to the CS10 condition, considered to be a positive control. However, the viability remains satisfactory (>90%), while the CS10 condition is stable.

For batch 4, the CS10 and 10% DMSO conditions are not different from one another and relative to T0, while the 3.5% DMSO arm exhibits viabilities which tend to be lower than the 10% DMSO reference arm.

For batches 3 and 2, the 2 formulations tested are not different from T0 and 10% DMSO.

Finally, the Differences are Small Between the Different Formulations, so the Post-Thawing Viability is not a Decisive Criterion.

Viabilities at Post-Thawing

| Batch 1: | | | | | |
|---|---|---|---|---|---|
| | | CS10 | | 3.5% DMSO | |
| Post-thawing | T0 | 2A | 2B | 4A | 4B |
| % viability | 96.9 | 95.0 | 95.3 | 92.9 | 93.5 |
| % T0 | | 98.0% | 98.3% | 95.9% | 96.5% |
| Mean | | 98.2 | | 96.2 | |
| Variance | | 0.04 | | 0.18 | |
| F-Test | | | | 0.30 | |
| T-Test | | | | 0.03 | |

| Batch 2: | | | | | |
|---|---|---|---|---|---|
| | | CS10 | | 3.5% DMSO | |
| Post-thawing | T0 | 2A | 2B | 4A | 4B |
| % viability | 95.9 | 93.2 | 96.2 | 95.2 | 95.5 |
| % T0 | | 97.2% | 100.3% | 99.3% | 99.6% |
| Mean | | 98.7 | | 99.4 | |
| Variance | | 4.50 | | 0.04 | |
| F-Test | | | | 0.06 | |
| T-Test | | | | 0.71 | |

| Batch 3: | | | | | | | |
|---|---|---|---|---|---|---|---|
| | | 10% DMSO | | CS10 | | 3.5% DMSO | |
| Post-thawing | T0 | 1A | 1B | 2A | 2B | 4A | 4B |
| % viability | 95.0 | 90.3 | 91.6 | 95.6 | 96.4 | 92.6 | 93.0 |
| % T0 | | 95.1% | 96.4% | 100.6% | 101.5% | 97.5% | 97.9% |
| Mean | | 95.7 | | 101.1 | | 97.7 | |
| Variance | | 0.84 | | 0.32 | | 0.08 | |
| F-Test | | | | 0.35 | | 0.19 | |
| T-Test | | | | 0.02 | | 0.11 | |

Batch 4:

| Post-thawing | T0 | 10% DMSO | | CS10 | | 3.5% DMSO | |
|---|---|---|---|---|---|---|---|
| | | 1A | 1B | 2A | 2B | 4A | 4B |
| % viability | 83.1 | 87.7 | 85.3 | 88.1 | 90.5 | 79.3 | 75.5 |
| % T0 | | 105.5% | 102.6% | 106.0% | 108.9% | 95.4% | 90.9% |
| Mean | | 104.1 | | 107.5 | | 93.1 | |
| Variance | | 2.88 | | 2.88 | | 7.22 | |
| F-Test | | | | 0.50 | | 0.36 | |
| T-Test | | | | 0.24 | | 0.06 | |

The analysis of the viability of the cells after 4 hours at room temperature in their primary container and their freezer formulation makes it possible to evaluate the thawed stability of the cells (simulates conditions of handling, transport and waiting before injection into the patient under real circumstances). It demonstrates a moderate decrease in the viability percentages for the 4 arms, of less than 20% of T0, which is acceptable.

For arm 3, statistical analysis shows a drop in viability only for batch 4.

Viabilities at 4 h Post-Thawing:

Batch 1:

| 4 h post-thawing | T0 | CS10 | | 3.5% DMSO | |
|---|---|---|---|---|---|
| | | 2A | 2B | 4A | 4B |
| % viability | 96.9 | 93.4 | 94.6 | 89.2 | 92.2 |
| % T0 | | 96.4% | 97.6% | 92.1% | 95.1% |
| Mean | | 97.0 | | 93.6 | |
| Variance | | 0.72 | | 4.50 | |

-continued

Batch 1:

| 4 h post-thawing | T0 | CS10 | | 3.5% DMSO | |
|---|---|---|---|---|---|
| | | 2A | 2B | 4A | 4B |
| F-Test | | | | 0.24 | |
| T-Test | | | | 0.18 | |

Batch 2:

| 4 h post-thawing | T0 | CS10 | | 3.5% DMSO | |
|---|---|---|---|---|---|
| | | 2A | 2B | 4A | 4B |
| % viability | 95.9 | 96.4 | 95.7 | 93.1 | 95.6 |
| % T0 | | 100.5% | 99.8% | 97.1% | 99.7% |
| Mean | | 100.2 | | 98.4 | |
| Variance | | 0.25 | | 3.13 | |
| F-Test | | | | 0.17 | |
| T-Test | | | | 0.32 | |

Batch 3:

| 4 h post-thawing | T0 | 10% DMSO | | CS10 | | 3.5% DMSO | |
|---|---|---|---|---|---|---|---|
| | | 1A | 1B | 2A | 2B | 4A | 4B |
| % viability | 95.0 | 85.8 | 93.9 | 95.0 | 95.7 | 92.9 | 94.1 |
| % T0 | | 90.3% | 98.8% | 100.0% | 100.7% | 97.8% | 99.1% |
| Mean | | 94.6 | | 100.4 | | 98.4 | |
| Variance | | 32.81 | | 0.25 | | 0.72 | |
| F-Test | | | | 0.05 | | 0.09 | |
| T-Test | | | | 0.31 | | 0.47 | |

Batch 4:

| 4 h post-thawing | T0 | 10% DMSO | | CS10 | | 3.5% DMSO | |
|---|---|---|---|---|---|---|---|
| | | 1A | 1B | 2A | 2B | 4A | 4B |
| % viability | 83.1 | 80.9 | 81.5 | 82.5 | 83.9 | 69.7 | 69.3 |
| % T0 | | 97.4% | 98.1% | 99.3% | 101.0% | 83.9% | 83.4% |
| Mean | | 97.7 | | 100.1 | | 83.6 | |
| Variance | | 0.18 | | 0.98 | | 0.08 | |
| F-Test | | | | 0.26 | | 0.37 | |
| T-Test | | | | 0.12 | | 0.00 | |

Analysis of the Phenotype

An analysis of the phenotype was carried out in order to determine the stability of the myoblasts in the product. For the first 3 batches, the percentages found are identical to T0 and are not significantly different from the reference arm. For batch 4, statistical analysis demonstrates significantly lower percentages for the cells formulated in 3.5% DMSO. Phenotypes:

Batch 1:

|  | T0 | CS10 | | 3.5% DMSO | |
|---|---|---|---|---|---|
|  |  | 2A | 2B | 4A | 4B |
| CD45−/CD90+/CD56+ | 38.18 | 36.47 | 39.41 | 31.14 | 32.34 |
| % T0 |  | 95.5% | 103.2% | 81.6% | 84.7% |
| Mean |  | 99.4 | | 83.1 | |
| Variance |  | 4.32 | | 0.72 | |
| F-Test |  | | | 0.25 | |
| T-Test |  | | | 0.06 | |

Batch 2:

|  | T0 | CS10 | | 3.5% DMSO | |
|---|---|---|---|---|---|
|  |  | 2A | 2B | 4A | 4B |
| CD45−/CD90+/CD56+ | 18.17 | 15.09 | 16.08 | 15.31 | 15.14 |
| % T0 |  | 83.0% | 88.5% | 84.3% | 83.3% |
| Mean |  | 85.8 | | 83.8 | |
| Variance |  | 0.49 | | 0.01 | |
| F-Test |  | | | 0.11 | |
| T-Test |  | | | 0.55 | |

Batch 3:

|  | T0 | 10% DMSO | | CS10 | | 3.5% DMSO | |
|---|---|---|---|---|---|---|---|
|  |  | 1A | 1B | 2A | 2B | 4A | 4B |
| CD45−/CD90+/CD56+ | 39.69 | 38.66 | 39.81 | 39.69 | 39.56 | 37.1 | 37.01 |
| % T0 |  | 97.4% | 100.3% | 100.0% | 99.7% | 93.5% | 93.2% |
| Mean |  | 98.9 | | 99.8 | | 93.4 | |
| Variance |  | 0.66 | | 0.01 | | 0.00 | |
| F-Test |  | | | 0.07 | | 0.05 | |
| T-Test |  | | | 0.57 | | 0.16 | |

Batch 4:

|  | T0 | 10% DMSO | | CS10 | | 3.5% DMSO | |
|---|---|---|---|---|---|---|---|
|  |  | 1A | 1B | 2A | 2B | 4A | 4B |
| CD45−/CD90+/CD56+ | 64.81 | 61.42 | 62.12 | 65.17 | 61.89 | 54.81 | 52.49 |
| % T0 |  | 94.8% | 95.8% | 100.6% | 95.5% | 84.6% | 81.0% |
| Mean |  | 95.3 | | 98.0 | | 82.8 | |
| Variance |  | 0.24 | | 5.38 | | 2.69 | |
| F-Test |  | | | 0.13 | | 0.19 | |
| T-Test |  | | | 0.40 | | 0.02 | |

Analysis of the Proliferation of the Cells

Batch 1:

|  | T0 | CS10 | | 3.5% DMSO | |
|---|---|---|---|---|---|
|  |  | 2A | 2B | 4A | 4B |
| Amount of cells N-1 | 15 000 | 15 000 | 15 000 | 15 000 | 15 000 |
| Concentration | 142 000 | 126 000 | 102 000 | 126 000 | 51 500 |
| Volume | 0.35 | 0.275 | 0.275 | 0.275 | 0.275 |
| Amount of cells N | 49 700 | 34 650 | 28 050 | 34 650 | 14 163 |
| Amplification factor | 3.31 | 2.31 | 1.87 | 2.31 | 0.94 |
| % T0 |  | 69.7% | 56.4% | 69.7% | 28.5% |
| Mean |  | 63.1 | | 49.1 | |
| Variance |  | 0.10 | | 0.93 | |
| F-Test |  | | | 0.20 | |
| T-Test |  | | | 0.58 | |

Batch 2:

|  | T0 | CS10 | | 3.5% DMSO | |
|---|---|---|---|---|---|
|  |  | 2A | 4A | 4A | 4A |
| Amount of cells N-1 | 15 000 | 15 000 | 15 000 | 15 000 | 15 000 |
| Concentration | 583 000 | 218 000 | 163 000 | 122 000 | 137 000 |
| Volume | 0.350 | 0.265 | 0.280 | 0.265 | 0.300 |
| Amount of cells N | 204 050 | 57 770 | 45 640 | 32 330 | 41 100 |
| Amplification factor | 13.6 | 3.9 | 3.0 | 2.2 | 2.7 |
| % T0 |  | 28.3% | 22.4% | 15.8% | 20.1% |
| Mean |  | 25.3 | | 18.0 | |
| Variance |  | 0.33 | | 0.17 | |
| F-Test |  | | | 0.40 | |
| T-Test |  | | | 0.18 | |

| Batch 3: | | | | | | | |
|---|---|---|---|---|---|---|---|
| | | 10% DMSO | | CS10 | | 3.5% DMSO | |
| | T0 | 1A | 1B | 4A | 4A | 4A | 4B |
| Amount of cells N-1 | 15 000 | 15 000 | 15 000 | 15 000 | 15 000 | 15 000 | 15 000 |
| Concentration | 383 000 | 102 000 | 147 000 | 245 000 | 266 000 | 117 000 | 134 000 |
| Volume | 0.34 | 0.37 | 0.37 | 0.37 | 0.39 | 0.39 | 0.37 |
| Amount of cells N | 130 220 | 37 740 | 54 390 | 90 650 | 103 740 | 45 630 | 49 580 |
| Amplification factor | 8.7 | 2.5 | 3.6 | 6.0 | 6.9 | 3.0 | 3.3 |
| % T0 | | 29.0% | 41.8% | 69.6% | 79.7% | 35.0% | 38.1% |
| Mean | | 35.4 | | 74.6 | | 36.6 | |
| Variance | | 0.62 | | 0.38 | | 0.03 | |
| F-Test | | | | 0.42 | | 0.15 | |
| T-Test | | | | 0.04 | | 0.87 | |

| Batch 4: | | | | | | | |
|---|---|---|---|---|---|---|---|
| | | 10% DMSO | | CS10 | | 3.5% DMSO | |
| | T0 | 1A | 1B | 4A | 4A | 4A | 4B |
| Amount of cells N-1 | 15 000 | 15 000 | 15 000 | 15 000 | 15 000 | 15 000 | 15 000 |
| Concentration | 67 900 | 56 000 | 60 900 | 64 300 | 96 100 | 33 900 | 41 500 |
| Volume | 0.28 | 0.26 | 0.25 | 0.25 | 0.25 | 0.25 | 0.25 |
| Amount of cells N | 19 012 | 14 560 | 15 225 | 16 075 | 24 025 | 8 475 | 10 375 |
| Amplification factor | 1.3 | 1.0 | 1.0 | 1.1 | 1.6 | 0.6 | 0.7 |
| % T0 | | 76.6% | 80.1% | 84.6% | 126.4% | 44.6% | 54.6% |
| Mean | | 78.3 | | 105.5 | | 49.6 | |
| Variance | | 0.00 | | 0.14 | | 0.01 | |
| F-Test | | | | 0.05 | | 0.21 | |
| T-Test | | | | 0.33 | | 0.03 | |

The proliferation tests were carried out with different incubation times:

Batch 1: 3 days of proliferation.
Batch 2: 5 days of proliferation.
Batch 3: 5 days of proliferation.
Batch 4: 3 days of proliferation.

Firstly, the analysis of the results demonstrates that the potential for proliferation of the cells is diminished after freezing. Indeed, the percentages of T0 vary greatly. The amplification factors of the cells formulated in 3.5% DMSO are not significantly different from the reference arms. However, for the $4^{th}$ cycle, the amplification factor of the cells of arm 3 is significantly lower than that of arm 1.

Conclusion of the Study

The present freezing study was therefore carried out on 4 batches of human myoblasts from different donors. Among the criteria studied, the conclusions are;

Viability of the cells. The cryopreservation of the myoblasts is effective in 3.5% DMSO formulation in terms of cell viability, because it is always greater than 80% of T0. The results obtained at 4 h post-thawing are reasonable, and validate clinical use.

Proliferation test. Freezing the myoblasts leads to an inherent decrease in the proliferation capacity of the cells, reflected in lower amplification factors than T0. This decrease is common to all the arms. This phenomenon, commonly observed in the laboratory, is not a criterion for excluding the freezing formulations.

Phenotype. The 3.5% DMSO freezing formulation perfectly preserves the percentage of cells of interest (myoblasts).

EXAMPLE 2: TESTS OF THE FORMULATION ACCORDING TO THE INVENTION FOR CRYOPRESERVING BLOOD MONONUCLEAR CELLS (BMCS)

The following formulation, named 3.5% DMSO, was prepared:

3.5% DMSO+1 mM L-cysteine+0.1 M trehalose+4% HA.

It requires an incubation time of 15 minutes maximum at 4° C. before freezing.

This complex formulation is combined with an automated temperature drop cycle carried out by means of a CRF (programmed freezer) which enables a complex drop in temperature according to a defined cycle. Down to −40° C. the cells are considered to be sensitive: the drop in temperature is slow and gradual to enable the formation of regular crystals. Below this threshold, the product is considered to be stable and the drop in temperature is rapid down to the storage temperature of −150° C. maximum (gaseous or liquid nitrogen).

Context of the Study

During the study of freezing of BMCs, 2 cycles were carried out, the characteristics of which are presented in the following table:

| Cycle (batch no.) | Starting material |
| --- | --- |
| 1 (16Pi00230) | Ring from cytapheresis donation kit |
| 2 (16Pi00231) | Ring from cytapheresis donation kit |

For the two cycles, the BMCs were isolated from the cytapheresis donation kit ring, after Ficoll. After 24 h incubation in a flask, enabling the adhesion of the monocytes, the BMCs were frozen at a concentration of $20 \times 10^6$ cells/ml by CRF.

In order to demonstrate the effectiveness of the freezing formulations, 3 arms are carried out. For each arm, 2 1 ml vials were thawed for testing.

|  | Arm 1 | Arm 2 | Arm 3 |
| --- | --- | --- | --- |
| Freezing Vials | 10% DMSO 1A and 1B | CS10* 2A and 2B | 3.5% DMSO 4A and 4B |

*CS10: Cryostor 10, commercial freezing formulation

Evaluation Criteria

With the aim of evaluating the effectiveness of the freezing formulations, different criteria, presented in the following table, were evaluated in comparison with the control before freezing (T0) and with the frozen references 10% DMSO and CS10. The results obtained were expressed in % of T0.

| T0 | Post-thawing | Purpose |
| --- | --- | --- |
| Viability | Post-thawing viability (measured within the hour) Viability at 4 h post-thawing | Primary criterion, which reflects the freezing effectiveness correlated with the presence of impurities (dead cells, debris, aggregates) which are often the cause of side-effects in patients. The viability of the cells after 4 hours at room temperature in the formulation tested makes it possible to evaluate the thawed stability (this time is necessary for handling, transport and injection of the cells under clinical conditions). |
| Phenotype | | Characterization of the cellular sub-populations, in particular the cells of interest and their relative importance. This is because the freezing/thawing cycle may specifically affect some more sensitive sub-types and alter the balance of the injected product (increase in cellular impurities, for example). |
| CFSE proliferation test | | Determining the amplification capacity of the cells = capacity for recovery, correlated to their metabolic activity. |
| Degranulation test | | Functional test for determining the immune potential of CD8+ T lymphocytes (IFNg synthesis and release of cytotoxic granules) |

The different freezing arms were compared by a test T. The reference freezing formulation 10% DMSO+4% HA (arm 1, negative control) commonly used within laboratories served as reference for the statistical analysis.

During the statistical analysis, the uniformity of the variances was estimated by Fisher's test (F-test, uniform variance if $p > 0.05$) and, depending on the result, a test of equality of means with two observations of equal or different variances was carried out. The means are significantly different if $p < 0.05$.

Analysis of the Viability of the Cells

For each batch, the analysis of the post-thawing viability demonstrates that the percentages obtained on thawing are equivalent to T0 for arms 1 and 2 (>96.0% of T0). It should be noted that the viability of conditions 1 and 2 is stable relative to T0.

For the batch 16Pi00230, arm 2 does not have any difference to arm 1.

Arm 3 of the 2 batches demonstrates lower viabilities (mean of 89.0% of T0). This trend is confirmed by statistical analysis, which demonstrates a significantly lower viability for 3.5% DMSO compared to 10% DMSO.

Table of analysis of the viability of the BMCs at 0 h post-thawing

| | | 16Pi00230 | | | | | |
| --- | --- | --- | --- | --- | --- | --- | --- |
| | | 10% DMSO | | CS10 | | 3.5% DMSO | |
| Post-thawing | T0 | 1A | 1B | 2A | 2B | 4A | 4B |
| Viability | 93.5 | 91.6 | 93.6 | 92.6 | 93.4 | 81.2 | 85.2 |
| % T0 | | 98.0% | 100.1% | 99.0% | 99.9% | 86.8% | 91.1% |
| Mean | | 99.0% | | 99.5% | | 89.0% | |
| Variance | | 2.00 | | 0.32 | | 8.00 | |
| F-Test | | | | 0.24 | | 0.30 | |
| T-Test | | | | 0.75 | | 0.05 | |

Table of analysis of the viability of the BMCs at 0 h post-thawing

| | | 16Pi00231 | | | | | |
|---|---|---|---|---|---|---|---|
| | | 10% DMSO | | CS10 | | 3.5% DMSO | |
| Post-thawing | T0 | 1A | 1B | 2A | 2B | 4A | 4B |
| Viability | 89.4 | 87.2 | 86.6 | 87.1 | 86 | 79.6 | 79.1 |
| % T0 | | 97.5% | 96.9% | 97.4% | 96.2% | 89.0% | 88.5% |
| Mean | | 97.2% | | 96.8% | | 88.8% | |
| Variance | | 0.18 | | 0.61 | | 0.13 | |
| F-Test | | | | 0.32 | | 0.44 | |
| T-Test | | | | 0.63 | | 0.00 | |

The analysis of the viability at 4 h post-thawing demonstrates a moderate decrease in the viability percentages for the 3 arms relative to T0, of less than or equal to 12%. At this stage, the 3.5% DMSO formulation does not differ from the 10% DMSO formulation for the batch 16Pi00230, but is significantly inferior for the batch 16Pi00231.

Table of analysis of the viability of the BMCs at 4 h post-thawing

| | | 16Pi00230 | | | | | |
|---|---|---|---|---|---|---|---|
| | | 10% DMSO | | CS10 | | 3.5% DMSO | |
| 4 h Post-thawing | T0 | 1A | 1B | 2A | 2B | 4A | 4B |
| Viability | 93.5 | 84.2 | 84.7 | 88.9 | 86.2 | 83.4 | 82.3 |
| % T0 | | 90.1% | 90.6% | 95.1% | 92.2% | 89.2% | 88.0% |
| Mean | | 90.3% | | 93.6% | | 88.6% | |
| Variance | | 0.13 | | 3.65 | | 0.61 | |
| F-Test | | | | 0.12 | | 0.27 | |
| T-Test | | | | 0.15 | | 0.12 | |

| | | 16Pi00231 | | | | | |
|---|---|---|---|---|---|---|---|
| | | 10% DMSO | | CS10 | | 3.5% DMSO | |
| 4 h Post-thawing | T0 | 1A | 1B | 2A | 2B | 4A | 4B |
| Viability | 89.4 | 88.5 | 87.2 | 87.3 | 86.1 | 81.4 | 83.2 |
| % T0 | | 99.0% | 97.5% | 97.7% | 96.3% | 91.1% | 93.1% |
| Mean | | 98.3% | | 97.0% | | 92.1% | |
| Variance | | 0.84 | | 0.72 | | 1.62 | |
| F-Test | | | | 0.47 | | 0.40 | |
| T-Test | | | | 0.32 | | 0.04 | |

Analysis of the Proliferation of the Cells by CFSE Test

This immunolabeling method aims to measure the proliferation of the cells by observing the extinguishment of an intracellular stain, CFSE (CarboxyFluorescein diacetate Succinimidyl Ester), which is diluted by the division of the stained parent cell into 2 daughter cells. It reflects the functional state of the cells.

For each of the batches, the test demonstrates the capacity of the thawed cells to proliferate, for all the arms. Statistical analysis concludes that there is no significant difference between the arms frozen in CS10 and 3.5% DMSO (for the batch 16Pi00230 only) versus 10% DMSO. However, the tested formulation and CS10 give more uniform results (low variance over the duplicates) while the 10% DMSO control is very variable (standard deviation=14.5% for the batch 16Pi00230).

For the batch 16Pi00231, the results obtained for the cells frozen in 3.5% DMSO are inferior to T0 and to the 10% DMSO condition.

Table of analysis of the proliferation of the BMCs post-thawing

| | | 16Pi00230 | | | | | |
|---|---|---|---|---|---|---|---|
| | | 10% DMSO | | CS10 | | 3.5% DMSO | |
| | T0 | 1A | 1B | 2A | 2B | 4A | 4B |
| % of proliferating | 92.0 | 93.6 | 73.0 | 92.1 | 96.5 | 91.2 | 91.0 |

Table of analysis of the proliferation of the BMCs post-thawing

| cells (ratio between T48 h and T0 h) | | | | | | | |
|---|---|---|---|---|---|---|---|
| % T0 | | 101.7% | 79.3% | 100.0% | 104.9% | 99.0% | 98.8% |
| Mean | | 90.5% | | 102.5% | | 98.9% | |
| Variance | | 212.18 | | 9.68 | | 0.002 | |
| F-Test | | | | 0.13 | | 0.01 | |
| T-Test | | | | 0.41 | | 0.59 | |

| | | 16Pi00231 | | | | | |
|---|---|---|---|---|---|---|---|
| | | 10% DMSO | | CS10 | | 3.5% DMSO | |
| | T0 | 1A | 1B | 2A | 2B | 4A | 4B |
| % of proliferating cells (ratio between T48 h and T0 h) | 96.0 | 92.9 | 96.9 | 95.4 | 92.9 | 70.5 | 71.5 |
| % T0 | | 96.9% | 101.0% | 99.4% | 96.8% | 73.5% | 74.5% |
| Mean | | 98.9% | | 98.1% | | 74.0% | |
| Variance | | 8.00 | | 3.23 | | 0.45 | |
| F-Test | | | | 0.36 | | 0.15 | |
| T-Test | | | | 0.77 | | 0.01 | |

Analysis of the Degranulation Test

The degranulation test makes it possible to evaluate the immune capacity of the cells (in particular the CD8+ cytotoxic effector population) in response to a CD3-CD28 activation signal imitated by beads.

The percentage of degranulating cells is diminished in all the frozen conditions relative to T0.

For the batch 16Pi00230, the comparison of the different conditions with one another does not demonstrate a significant difference, because the 10% DMSO reference is also highly variable (=16.2±6.7).

For the batch 16Pi00231, in the case of conditions 1 and 2, this decrease is moderate and acceptable, unlike the 3.5% DMSO condition in which the drop in immune capacity is drastic (from 22.3% before freezing to 6.1%). For arms 1 and 2, the percentages of proliferating cells are stable (approximately 20%).

Table of analysis of the degranulation test of the BMCs post-thawing

| | | 16Pi00230 | | | | | |
|---|---|---|---|---|---|---|---|
| | | 10% DMSO | | CS10 | | 3.5% DMSO | |
| | T0 | 1A | 1B | 2A | 2B | 4A | 4B |
| % CD3+ CD8+ CD107+ IFN+ | 49.0 | 11.5 | 20.9 | 8.5 | 10.6 | 5.9 | 10.3 |
| % T0 | | 23.4% | 42.7% | 17.3% | 21.6% | 12.0% | 21.0% |
| Mean | | 33.0% | | 19.4% | | 16.5% | |
| Variance | | 44.94 | | 2.21 | | 9.72 | |
| F-Test | | | | 0.14 | | 0.28 | |
| T-Test | | | | 0.30 | | 0.26 | |

| | | 16Pi00231 | | | | | |
|---|---|---|---|---|---|---|---|
| | | 10% DMSO | | CS10 | | 3.5% DMSO | |
| | T0 | 1A | 1B | 2A | 2B | 4A | 4B |
| % CD3+ CD8+ CD107+ IFN+ | 22.3 | 22.9 | 20.9 | 20.6 | 19.7 | 4.9 | 7.3 |
| % T0 | | 102.9% | 93.7% | 92.4% | 88.6% | 22.0% | 33.0% |
| Mean | | 98.3% | | 90.5% | | 27.5% | |
| Variance | | 2.08 | | 0.36 | | 3.00 | |
| F-Test | | | | 0.25 | | 0.44 | |
| T-Test | | | | 0.26 | | 0.01 | |

Analysis of the Phenotype

It makes it possible to determine the cellular composition of the BMCs given as percentages.

Among the total cells:
  Hematopoietic cells (CD45+)
  Non-hematopoietic cellular impurities (CD45−)
Among the CD45+ cells:
  CD45+/3+T lymphocytes
  CD45+/3+/8+ cytotoxic T lymphocytes
  CD45+/3+/4+ helper T lymphocytes
  CD45+/3+/16+$^{and}/_{or}$ 56+NK (Natural Killer)
  CD45+/19+/3-B lymphocytes
  CD45+/14+/3-monocytes The different formulations have different preservation properties depending on the sub-population under consideration: the 3.5% DMSO formulation is the most effective for preserving monocytes and B lymphocytes. A decrease in CD4 and CD8 T lymphocytes is observed (−14.9% in comparison to T0).

The preservation of the NKs is correlated to the % of DMSO in the formulations. A dose-dependent effect is observed from the intermediate 3.5% DMSO formulation (75.0%) to the 10% DMSO formulation (84.2%). The CS10 condition containing 10% DMSO is not significantly different from the 10% DMSO.

Summary table per batch of the results obtained for the BMC phenotyping

| | 16Pi00230 | | | | | | |
|---|---|---|---|---|---|---|---|
| | | 10% DMSO | | CS 10 | | 3.5% DMSO | |
| Cell type | T0 | 1A | 1B | 2A | 2B | 4A | 4B |
| CD45+ | 94.2 | 97.3 | 96.5 | 96.4 | 96.0 | 96.1 | 96.5 |
| CD45− | 5.8 | 2.7 | 3.5 | 3.6 | 4.0 | 3.9 | 3.5 |
| CD3+ T ly | 59.2 | 50.1 | 58.4 | 57.3 | 61.3 | 54.5 | 55.7 |
| CD8+ cytotoxic T ly | 15.3 | 15.5 | 13.5 | 14.8 | 15.1 | 16.9 | 13.2 |
| CD4+ helper T ly | 42.7 | 32.8 | 36.2 | 40.7 | 44.6 | 35.2 | 28.6 |
| CD16+ and/or CD56+ NK | 18.3 | 14.0 | 14.8 | 12.2 | 14.7 | 10.9 | 12.5 |
| CD19+ B ly | 5.1 | 7.9 | 8.5 | 7.5 | 7.3 | 10.1 | 10.1 |
| CD45+ CD3− CD14+ monocyte | 3.6 | 4.7 | 5.0 | 5.2 | 4.0 | 7.5 | 11.9 |

| | 16Pi00231 | | | | | | |
|---|---|---|---|---|---|---|---|
| | | 10% DMSO | | CS 10 | | 3.5% DMSO | |
| Cell type | T0 | 1A | 1B | 2A | 2B | 4A | 4B |
| CD45+ | 92.8 | 97.3 | 96.7 | 96.3 | 95.3 | 94.6 | 94.2 |
| CD45− | 7.2 | 2.7 | 3.3 | 3.7 | 4.7 | 5.4 | 5.8 |
| CD3+ T ly | 68.7 | 66.7 | 67.7 | 67.1 | 68.9 | 51.8 | 54.1 |
| CD8+ cytotoxic T ly | 25.9 | 28.0 | 28.2 | 27.8 | 27.3 | 21.1 | 21.1 |
| CD4+ helper T ly | 42.1 | 37.9 | 38.8 | 38.7 | 40.9 | 29.9 | 32.3 |
| CD16+ and/or CD56+ NK | 12.4 | 10.8 | 11.4 | 10.9 | 10.2 | 10.4 | 10.9 |
| CD19+ B ly | 6.9 | 7.8 | 8.0 | 7.5 | 7.3 | 12.9 | 12.1 |
| CD45+ CD3− CD14+ monocyte | 5.3 | 4.9 | 4.9 | 4.7 | 4.7 | 8.6 | 8.3 |

T ly: T lymphocyte.
NK: Natural Killer.
B ly: B lymphocyte

The results obtained for each batch follow the same trend. Indeed, the values of T0 are close, and enable analysis of the combined means of the 2 batches. The table below presents these values as % of T0 (n=2 replicates over 2 batches, i.e. 4 values in total for the thawed conditions, T0 carried out in duplicate only).

TABLE of analysis of the phenotypes
Means expressed as % of T0 obtained over the 2 batches

| Cell type | 10% DMSO | CS10 | 3.5% DMSO |
|---|---|---|---|
| CD45+ | 103.7% | 102.7% | 102.0% |
| CD45− | 47.4% | 61.8% | 70.8% |
| CD3+ T ly | 94.6% | 99.6% | 85.1% |
| CD8+ cytotoxic T ly | 101.7% | 102.0% | 89.9% |
| CD4+ helper T ly | 85.9% | 97.2% | 74.3% |
| CD16+ and/or CD56+ NK | 84.2% | 79.4% | 75.0% |
| CD19+ B ly | 138.2% | 126.4% | 190.1% |
| CD45+ CD3− CD14+ monocyte | 114.4% | 108.6% | 214.9% |

Conclusion of the Study

The present freezing study was thus carried out on 2 batches of BMCs originating from cytapheresis rings from 2 different healthy patients. Among the criteria studied, the conclusions are:
  Viability of the cells. The cryopreservation of the BMCs is effective in the 3.5% DMSO formulation (moderate decrease of about 10% on 3.5% DMSO). The results obtained at 4 h post-thawing are satisfactory and permit clinical use.
  Proliferation test (CFSE). Freezing the BMCs in the 3.5% DMSO formulation does not adversely affect the proliferation capacity of the cells.
  Degranulation test. The immune capacity of the population of T lymphocytes within the BMCs is relatively variable and patient-dependent. The results of the first batch, which are highly variable, should be put into perspective (large decrease in functionality in all cases). While the results obtained post-thawing are poorer than those obtained for T0, the T lymphocytes retain a cytotoxic capacity.

Phenotype. The 3.5% DMSO freezing formulation shows a specific action: it preferentially preserves certain cell populations. Indeed, the 3.5% DMSO formulation is more effective in preserving NKs.

EXAMPLE 3: TESTS WITH THE FORMULATION ACCORDING TO THE INVENTION FOR CRYOPRESERVING MESENCHYMAL STEM CELLS (MSCS)

The following formulation, named 3.5% DMSO, was prepared:
3.5% DMSO+1 mM L-cysteine+0.1 M trehalose+4% human serum albumin (HA).

It requires an incubation time of 15 minutes maximum at 4° C. before freezing.

This complex formulation is combined with an automated temperature drop cycle carried out by means of a CRF (programmed freezer) which enables a complex drop in temperature according to a defined cycle. Down to −40° C. the cells are considered to be sensitive: the drop in temperature is slow and gradual to enable the formation of regular crystals. Below this threshold, the product is considered to be stable and the drop in temperature is rapid down to the storage temperature of −150° C. maximum (gaseous or liquid nitrogen).

Context of the Study

During the study, 2 cycles were carried out, the characteristics of which are presented in the following table:

| Cycles | Batch no. | Starting material | Comments |
|---|---|---|---|
| 1 | 62535836 | Vial pass 2 | Supplier: ATCC |
| 2 | 8900-101 | Vial pass 4 | Supplier: Thermo Scientific |

Each cycle corresponds to a batch of cells originating from a different donor. For these 2 cycles, a vial of MSCs originating from ATCC for cycle 1 and from Thermo Fisher Scientific for cycle 2 were thawed. The cells were amplified over several weeks then frozen by CRF at a concentration of:
1.2×10$^6$ cells/ml for cycle 1.
2.5×10$^6$ cells/ml for cycle 2.

In order to demonstrate the effectiveness of the freezing formulations, 3 arms were carried out. For each arm, 2 1 ml vials (duplicates) were thawed for testing.

|  | Arm 1 | Arm 2 | Arm 3 |
|---|---|---|---|
| Freezing | 10% DMSO** | CS10* | 3.5% DMSO |
| Vials | 1A and 1B | 2A and 2B | 4A and 4B |

*CS10: Cryostor 10, commercial freezing formulation (STEMCELL Technologies)
**10% DMSO + 4% HA.

Evaluation Criteria

With the aim of evaluating the effectiveness of the freezing formulations, various selective tests, presented in the following table, were carried out before freezing (referred to as T0) and after thawing. The results obtained on the thawed cells were compared to T0 and expressed in % relative to T0.

| T0 | Post-thawing | Aim |
|---|---|---|
| Viability | Post-thawing viability (within the hour) Viability at 4 h post-thawing | General criterion (primary criterion, often liberating, which enables the injection of the cells, often correlated to effectiveness and to side-effects (acellular impurities: debris, aggregates etc.)). |
|  | Phenotype | Characterization of the cellular sub-populations and the cells of interest. This is because the freezing/thawing cycle may specifically affect some more sensitive sub-types and alter the balance of the injected product (increase in cellular impurities). |
|  | Proliferation test | Determining the amplification factor of the cells, and hence their capacity for recovery, correlated to metabolic activity. |

The different arms were compared by statistical analysis. The reference formulation (arm 1) is 10% DMSO+4% HA.

During the statistical analysis, the uniformity of variances was analyzed by a Fisher's test (F-test; uniform variance if p>0.05). Then a test of equality of means with two equal or unequal variance observations was carried out. The means are not significantly different if p>0.05. The means are significantly different if p<0.05.

Results

Analysis of the Viability of the Cells

The analysis of the post-thawing viability demonstrates that the conditions tested are not different from T0 for all the frozen arms (values >98% of T0). The differences demonstrated by the statistical analysis are due to the variability of the test.

Summary table of the viability of the MSCs post-thawing (in % viability and in % relative to T0)

| Batch | post-thawing | T0 | 10% DMSO | | CS10 | | 3.5% DMSO | |
|---|---|---|---|---|---|---|---|---|
|  |  |  | 1A | 1B | 2A | 2B | 4A | 4B |
| 62535836 | % viability | 95.3% | 94.9% | 95.0% | 96.9% | 96.8% | 96.1% | 96.0% |
|  | % T0 |  | 99.6% | 99.7% | 101.7% | 101.6% | 100.8% | 100.7% |
| 8900-101 | % viability | 97.5% | 96.6% | 95.7% | 98.6% | 98.5% | 97.8% | 97.4% |
|  | % T0 |  | 99.1% | 98.2% | 101.1% | 101.0% | 100.3% | 99.9% |
|  | Mean |  | 99.1% | | 101.4% | | 100.4% | |
|  | F-Test |  | | | 0.12 | | 0.22 | |
|  | T-Test |  | | | 0.00 | | 0.02 | |

The analysis of the viability of the cells after 4 hours at room temperature in their primary container and their freezer formulation makes it possible to evaluate the thawed stability of the cells (simulation of real conditions of handling, transport and waiting before injection into the patient). It demonstrates stable percentages of viability for the 3 arms.

Table of analysis of the viability of the MSCs at 4 h post-thawing (in % viability and in % relative to T0)

| Batch | 4 h post-thawing | T0 | 10% DMSO | | CS10 | | 3.5% DMSO | |
|---|---|---|---|---|---|---|---|---|
| | | | 1A | 1B | 2A | 2B | 4A | 4B |
| 62535836 | % viability | 95.3% | 95.6% | 94.6% | 96.3% | 96.5% | 92.9% | 92.9% |
| | % T0 | | 100.3% | 99.3% | 101.0% | 101.3% | 97.5% | 97.5% |
| 8900-101 | % viability | 97.5% | 92.4% | 90.3% | 97.6% | 95.6% | 94.5% | 92.5% |
| | % T0 | | 94.8% | 92.6% | 100.1% | 98.1% | 96.9% | 94.9% |
| | Mean | | 96.7% | | 100.1% | | 96.7% | |
| | F-Test | | | | 0.84 | | 0.05 | |
| | T-Test | | | | 0.14 | | 0.98 | |

For the 2 batches, after 4 h post-thawing, the variations are small (between 92 and 101% of T0). After comparative analysis of the 3.5% DMSO formulation, no significant difference is demonstrated relative to the reference (10% DMSO) and also to the positive control (CS10). The formulation has a preservation capacity close to CS10.

In detail, the 10% DMSO condition is the most variable between the two batches of cells tested, while the CS10 formulation is the most stable.

Finally, the differences are small between the different formulations, so the post-thawing viability is not a decisive criterion.

Analysis of the Phenotype

Phenotyping was carried out in order to determine the stability of the population of MSCs in the thawed product. For the 2 batches (62/535,836 and 8900-101), the percentages obtained are not significantly different from T0. The amount of cells of interest is therefore not affected by the freezing/thawing process.

Summary table of the results obtained for the MSC phenotyping (in % relative to T0)

| Batch | phenotype | T0 | 10% DMSO | | CS10 | | 3.5% DMSO | |
|---|---|---|---|---|---|---|---|---|
| | | | 1A | 1B | 2A | 2B | 4A | 4B |
| 62535836 | CD73+/90+/105+ | 96.9% | 98.5% | 98.6% | 98.6% | 98.1% | 99.0% | 99.2% |
| | % T0 | | 101.7% | 101.8% | 101.8% | 101.2% | 102.2% | 102.4% |
| 8900-101 | CD73+/90+/105+ | 100.0% | 100.0% | 99.9% | 100.0% | 100.0% | 99.9% | 99.9% |
| | % T0 | | 100.0% | 99.9% | 100.0% | 100.0% | 99.9% | 99.9% |
| | Mean | | 100.8% | | 100.7% | | 101.1% | |
| | F-Test | | | | 0.42 | | 0.32 | |
| | T-Test | | | | 0.91 | | 0.77 | |

Analysis of the Proliferation of the Cells

The principle of the proliferation test consists in seeding 50 000 cells in a 6-well plate and in counting the number of cells obtained after 7 days in proliferation conditions without changing the medium. The phase of amplification of the cells took place in the same medium as that of the pre-freezing culturing phase.

For the 2 cycles, the proliferation tests failed over the T0 conditions. In the first case, the cells inexplicably became detached (stress), and in the 2nd case, the cells stagnated. Due to this, the arm formulated in 3.5% DMSO is compared only to the control arm (10% DMSO and CS10).

Summary table of the results obtained for the MSC proliferation tests

| Batch | proliferation test | 10% DMSO | | CS10 | | 3.5% DMSO | |
|---|---|---|---|---|---|---|---|
| | | 1A | 1B | 2A | 2B | 4A | 4B |
| 62535836 | Amplification | 1.8 | 1.7 | 2.0 | 2.4 | 1.7 | 1.6 |
| 8900-101 | factor | 2.2 | 2.1 | 2.4 | 2.3 | 2.3 | 2.0 |
| | Mean | 2.0 | | 2.3 | | 1.9 | |
| | F-Test | | | 0.35 | | 0.36 | |
| | T-Test | | | 0.11 | | 0.77 | |

The proliferation capacity of the cells is preserved for each thawed condition. Statistical analysis does not demonstrate any significant difference between them. Consequently, the 3.5% DMSO formulation is equivalent to the references.

Conclusion of the Study

The present study, carried out on 2 batches of human MSCs originating from commercial vials, and recultured, demonstrates that:

Viability of the cells. The cryopreservation of the MSCs is effective in 3.5% DMSO formulation in terms of cell viability, because it is always greater than 98% of T0. Moreover, it is equivalent to CS10 (positive control). The results obtained at 4 h post-thawing are excellent (no reduction in viability) and validate clinical use.

Proliferation test. Freezing the MSCs with different formulations does not affect the proliferation capacity of the cells. However, in the absence of T0, it is not possible to qualify this. The amplification factors obtained for the cells formulated in 3.5% DMSO are not different from the controls. This demonstrates the equivalence of the formulations with CS10 (control).

Phenotype. The 3.5% DMSO freezing formulation perfectly preserves the percentage of cells of interest (MSCs).

The 2 batches of MSCs were cultured in 2 different ways, the first batch received from ATCC was amplified for 1 and a half months under the conditions recommended by ATCC (ATCC medium+growth kit), the other, originating from Thermo Fischer, for 3 weeks under conditions of DMEM+ low glucose concentration+10% fetal calf serum (FCS). These differences do not have an impact on the results, since the trends are the same for the 2 cycles.

EXAMPLE 4: TESTS WITH THE FORMULATION ACCORDING TO THE INVENTION FOR CRYOPRESERVING FIBROBLASTS

The following formulation, named 3.5% DMSO, was prepared:
3.5% DMSO+1 mM L-cysteine+0.1 M trehalose+4% human serum albumin (HA).

It requires an incubation time of 15 minutes maximum at 4° C. before freezing.

This complex formulation is combined with an automated temperature drop cycle carried out by means of a CRF (programmed freezer) which enables a complex drop in temperature according to a defined cycle. Down to −40° C. the cells are considered to be sensitive: the drop in temperature is slow and gradual to enable the formation of regular crystals. Below this threshold, the product is considered to be stable and the drop in temperature is rapid down to the storage temperature of −150° C. maximum (gaseous or liquid nitrogen).

Context of the Study

During the study, 2 cycles were carried out, the characteristics of which are presented in the following table:

| Cycles | Batch no. | Starting material |
|---|---|---|
| 1 | FPCCC12080 | Vial pass 2 |
| 2 | FPCCC12081 | Vial pass 4 |

For these 2 cycles, vials of fibroblasts originating from different healthy patients were thawed. The cells were amplified then frozen at the concentration of $5 \times 10^6$ cells/ml by CRF.

In order to demonstrate the effectiveness of the freezing formulations, 3 arms were carried out. For each arm, 2 1 ml vials were thawed for testing.

|  | Arm 1 | Arm 2 | Arm 3 |
|---|---|---|---|
| Freezing Vials | 10% DMSO** 1A and 1B | CS10* 2A and 2B | 3.5% DMSO 4A and 4B |

*CS10: Cryostor 10, commercial freezing formulation (STEMCELL Technologies)
**10% DMSO + 4% HA.

Evaluation Criteria

With the aim of evaluating the effectiveness of the freezing formulations, various selective tests, presented in the following table, were carried out before freezing (T0) and after thawing (arms 1 to 3). The results obtained on the thawed cells were compared to T0 and expressed in % relative to T0.

| T0 | Post-thawing | Aim |
|---|---|---|
| Viability | Post-thawing viability (within the hour) Viability at 4 h post-thawing | General primary criterion, often liberating, which enables or does not enable the injection to be correlated to effectiveness and to side-effects (increase in acellular impurities due to debris, aggregates etc.). |
|  | Phenotype | Characterization of the cellular subpopulations and in particular of the cells of interest. This is because the freezing/thawing cycle may specifically affect some more sensitive sub-types and alter the balance of the injected product (increase in cellular impurities). |
|  | Proliferation test | Determining the amplification factor of the cells, and hence their capacity for recovery, correlated to their metabolic/functional activity. |

The different arms were compared by statistical analysis. The reference formulation (arm 1) is 10% DMSO+4% HA.

During the statistical analysis, the uniformity of variances was carried out by a Fisher's test (F-test; uniform variance if $p > 0.05$). A test of equality of means with two equal variance observations was carried out in the case of uniform variance. In the case of non-uniform variance, a test of equality of means with two different variance observations was carried out. The means are not significantly different if $p > 0.05$. The means are significantly different if $p < 0.05$.

Results

Analysis of the Viability of the Cells

The post-thawing viability confirms the freezing effectiveness across all the arms (>99% of T0).

Table of analysis of the viability of the fibroblasts post-thawing (in % viability and in % relative to T0)

| Batch | post-thawing | T0 | 10% DMSO 1A | 10% DMSO 1B | CS10 2A | CS10 2B | 3.5% DMSO 4A | 3.5% DMSO 4B |
|---|---|---|---|---|---|---|---|---|
| FPCCC12080 | % viability | 98.3% | 98.6% | 98.2% | 98.4% | 97.2% | 96.7% | 98.2% |
|  | % T0 |  | 100.3% | 99.9% | 100.1% | 98.9% | 98.4% | 99.9% |
| FPCCC12081 | % viability | 98.3% | 97.7% | 98.1% | 98.5% | 97.8% | 97.6% | 97.7% |
|  | % T0 |  | 99.4% | 99.8% | 100.2% | 99.5% | 99.3% | 99.4% |
| Mean |  |  | 99.8% |  | 99.7% |  | 99.2% |  |
| F-Test |  |  |  |  | 0.22 |  | 0.21 |  |
| T-Test |  |  |  |  | 0.64 |  | 0.15 |  |

The analysis of the viability of the cells after 4 hours at room temperature in their primary container makes it possible to evaluate the thawed stability of the cells (simulation of real conditions of handling, transport and waiting before injection into the patient).

| | Table of analysis of the viability of the fibroblasts at 4 h post-thawing (in % viability and in % relative to T0) | | | | | | | |
|---|---|---|---|---|---|---|---|---|
| | 4 h post- | | 10% DMSO | | CS10 | | 3.5% DMSO | |
| Batch | thawing | T0 | 1A | 1B | 2A | 2B | 4A | 4B |
| FPCCC12080 | % viability | 98.3% | 98.1% | 98.3% | 97.0% | 97.3% | 98.2% | 98.2% |
| | % T0 | | 99.8% | 100.0% | 98.7% | 99.0% | 99.9% | 99.9% |
| FPCCC12081 | % viability | 98.3% | 96.1% | 95.5% | 97.9% | 97.1% | 96.7% | 96.3% |
| | % T0 | | 97.8% | 97.2% | 99.6% | 98.8% | 98.4% | 98.0% |
| | Mean | | 98.7% | | 99.0% | | 99.0% | |
| | F-Test | | | | 0.03 | | 0.29 | |
| | T-Test | | | | 0.69 | | 0.70 | |

At 4 h post-thawing, the viability of the cells remains stable (not significantly different from T0) for the 2 batches. The formulations are not toxic for the cells at room temperature.

The 3.5% DMSO formulation has the same preservation potential as 10% DMSO (reference) and CS10 (positive control), demonstrated by the absence of significant differences during statistical analysis.

Analysis of the Phenotype

Phenotyping was carried out in order to determine the stability of the population of fibroblasts in the product. The percentages found are stable relative to T0. The amount of cells of interest is therefore not affected by the freezing/thawing process.

| | Summary table of results obtained for the phenotype of the fibroblasts (in % relative to T0) | | | | | | | |
|---|---|---|---|---|---|---|---|---|
| | | | 10% DMSO | | CS10 | | 3.5% DMSO | |
| Batch | phenotype | T0 | 1A | 1B | 2A | 2B | 4A | 4B |
| FPCCC12080 | CD61+/73+/90+ | 99.6% | 99.7% | 99.6% | 99.3% | 99.7% | 99.7% | 99.8% |
| | % T0 | | 100.1% | 100.0% | 99.7% | 100.1% | 100.1% | 100.2% |
| FPCCC12081 | CD61+/73+/90+ | 98.0% | 99.8% | 99.7% | 99.7% | 99.9% | 99.9% | 99.8% |
| | % T0 | | 101.8% | 101.7% | 101.7% | 101.9% | 101.9% | 101.8% |
| | Mean | | 100.9% | | 100.9% | | 101.0% | |
| | F-Test | | | | 0.42 | | 0.50 | |
| | T-Test | | | | 0.95 | | 0.89 | |

Analysis of the Proliferation of the Cells

The principle of the proliferation test consists in seeding 50 000 cells per plate in a 6-well plate and in measuring the number of cells obtained after 3 days of incubation.

| | Summary table of results obtained for the tests of proliferation of the fibroblasts (in % relative to T0) | | | | | | | |
|---|---|---|---|---|---|---|---|---|
| | Proliferation | | 10% DMSO | | CS10 | | 3.5% DMSO | |
| Batch | test | T0 | 1A | 1B | 2A | 2B | 4A | 48 |
| FPCCC12080 | Amplification factor | 4.8 | 5.6 | 4.2 | 7.3 | 4.6 | 4.8 | 6.5 |
| | % T0 | | 116.3% | 86.6% | 150.4% | 95.3% | 99.0% | 134.9% |
| FPCCC12081 | Amplification factor | 1.9 | 3.0 | 3.2 | 2.5 | 2.7 | 1.7 | 2.0 |
| | % T0 | | 157.1% | 166.6% | 129.0% | 143.4% | 87.2% | 103.3% |
| | Mean | | 131.7% | | 129.5% | | 106.1% | |
| | F-Test | | | | 0.26 | | 0.18 | |
| | T-Test | | | | 0.93 | | 0.27 | |

According to the results obtained, the thawed cells preserve their proliferation capacity and do not exhibit any significant differences from one another.

Conclusion of the Study

The present freezing study was therefore carried out on 2 batches of human fibroblasts from different donors. Among the criteria studied, the conclusions are:
Viability of the cells. The cryopreservation of the fibroblasts is effective in 3.5% DMSO formulation in terms of cell viability, because it is always greater than 97% of T0. Moreover, it is equivalent to CS10 (positive control). The results obtained at 4 h post-thawing are satisfactory (no observable reduction in viability) and enable clinical use.
Proliferation test. The proliferation capacity of the fibroblasts is dependent on the batch in question. For the first batch, the cells are not affected by the freezing, which is reflected in amplification factors which are greater than or equal to T0 for the 3 arms. For the 2nd cycle, the degrees of amplification are better for the thawed cells.
Phenotype. The 3.5% DMSO freezing formulation effectively preserves the percentage of cells of interest (fibroblasts).

The invention claimed is:

1. A composition consisting of a medium consisting of:
a) human albumin,
b) at least one saccharide selected from disaccharides and trisaccharides,
c) DMSO and L-cysteine, and
d) cells for therapeutic purposes, with the exception of tumor-infiltrating lymphocytes,
said tumor-infiltrating lymphocytes being obtained by in vitro culture of tumor-infiltrating lymphocytes from a sample taken of in-transit, lymph-node or metastatic cutaneous nodules from a patient suffering from a stage 3 or 4 melanoma, said culture comprising the emergence of said tumor-infiltrating lymphocytes contained in the sample taken of in-transit, lymph-node or metastatic cutaneous nodules, then the stimulation of the tumor-infiltrating lymphocytes resulting from the emergence step, then finally the amplification of the stimulated tumor-infiltrating lymphocytes.

2. The composition as claimed in claim 1, wherein the saccharide is disaccharides.

3. The composition as claimed in claim 1, wherein the saccharide is a disaccharide selected from trehalose and sucrose.

4. The composition as claimed in claim 1, wherein the human albumin is present in an amount of between 2 and 10% by weight relative to the total weight of composition.

5. The composition as claimed in claim 1, wherein the saccharide is present at a concentration of between 0.05 M and 1 M.

6. The composition as claimed in claim 1, wherein the cells for therapeutic purposes are chosen from immune cells, human myoblasts, hematopoietic stem cells, mesenchymal stem cells, cardiac cells, fibroblasts and all other natural or genetically modified cells.

7. The composition as claimed in claim 1, wherein the saccharide is
trehalose.

8. A process for the cryopreservation of at least one sample of cells for therapeutic purposes, with the exception of tumor-infiltrating lymphocytes, comprising the following steps:
i) mixing the sample of cells for therapeutic purposes with a medium consisting of:
a) human albumin,
b) at least one saccharide selected from disaccharides and trisaccharides, and
c) DMSO and L-cysteine, then
ii) freezing the mixture obtained in step i),
said tumor-infiltrating lymphocytes being obtained by in vitro culture of tumor-infiltrating lymphocytes from a sample taken of in-transit, lymph-node or metastatic cutaneous nodules from a patient suffering from a stage 3 or 4 melanoma, said culture comprising the emergence of said tumor-infiltrating lymphocytes contained in the sample taken of in-transit, lymph-node or metastatic cutaneous nodules, then the stimulation of the tumor-infiltrating lymphocytes resulting from the emergence step, then finally the amplification of the stimulated tumor-infiltrating lymphocytes.

9. The cryopreservation process as claimed in claim 8, wherein the freezing ii) is carried out down to a temperature of between −100° C. and −180° C.

10. The cryopreservation process as claimed in claim 8, wherein the freezing ii) is carried out by placing the mixture obtained in i) in a container submerged in a mixture of isopropyl alcohol at +4° C., everything being brought to a temperature of between −70° C. and −100° C.

11. The cryopreservation process as claimed in claim 8, wherein the freezing ii) is carried out by means of a programmed freezer.

12. A method for the cryopreservation of at least one sample of cells for therapeutic purposes, with the exception of tumor-infiltrating lymphocytes, the method comprising:
providing a composition consisting of a medium consisting of:
a) human albumin,
b) at least one saccharide selected from disaccharides and trisaccharides, and
c) DMSO and L-cysteine,
said tumor-infiltrating lymphocytes being obtained by in vitro culture of tumor-infiltrating lymphocytes from a sample taken of in-transit, lymph-node or metastatic cutaneous nodules from a patient suffering from a stage 3 or 4 melanoma, said culture comprising the emergence of said tumor-infiltrating lymphocytes contained in the sample taken of in-transit, lymph-node or metastatic cutaneous nodules;
stimulating the tumor-infiltrating lymphocytes resulting from the emergence step; and
amplifying the stimulated tumor-infiltrating lymphocytes.

13. The composition of claim 4, wherein the human albumin is present in an amount of between 2.5 and 6% by weight relative to the total weight of composition.

14. The composition of claim 5, wherein the saccharide is present at a concentration of between 0.07 M and 0.5 M.

15. The composition of claim 7, wherein the human albumin is present in an amount of between 2.5 and 6% by weight.

16. The composition of claim 15, wherein the trehalose is present at a concentration of between 0.05 M and 0.5 M.

17. The composition of claim 16, wherein the DMSO and L-cysteine are present, respectively, in an amount of between 2 and 15% by weight and in a concentration of between 0.5 mM and 2 mM.

18. The cryopreservation process of claim 9, wherein the freezing ii) is carried out down to a temperature of between −140° C. and −160° C.

19. The composition as claimed in claim 2, comprising L-cysteine.

20. The composition as claimed in claim 6, wherein the immune cells are chosen from NK cells, monocytes, B lymphocytes, T lymphocytes, which are natural or genetically modified.

21. The composition as claimed in claim 20, wherein the T lymphocytes are chosen from regulatory T lymphocytes, cytotoxic T lymphocytes, helper T lymphocytes, and chimeric antigen receptor (CAR) T lymphocytes.

* * * * *